United States Patent [19]

Waynant et al.

[11] Patent Number: 5,359,685
[45] Date of Patent: Oct. 25, 1994

[54] FOCUSING TIPS FOR OPTICAL FIBERS

[75] Inventors: Ronald W. Waynant, Laurel; Morton Fink, Silver Spring, both of Md.

[73] Assignee: The United States of America as represented by the Department of Health and Human Services, Washington, D.C.

[21] Appl. No.: 718,666

[22] Filed: Jun. 21, 1991

[51] Int. Cl.⁵ .............................. G02B 6/32
[52] U.S. Cl. ........................ 385/35; 385/33; 385/93
[58] Field of Search ............ 350/96.18, 96.20; 385/35, 33, 34, 92, 93, 94, 15, 31

[56] References Cited

U.S. PATENT DOCUMENTS

| | | | |
|---|---|---|---|
| 3,327,712 | 6/1967 | Kaufman et al. | 128/398 |
| 3,843,865 | 10/1974 | Nath | 219/121 L |
| 4,169,664 | 10/1979 | Bailey | 351/23 |
| 4,290,667 | 9/1981 | Chown | 350/96.18 |
| 4,418,688 | 12/1983 | Loeb | 128/6 |
| 4,470,407 | 9/1984 | Hussein | 128/6 |
| 4,641,912 | 2/1987 | Goldenberg | 350/96.1 |
| 4,681,104 | 7/1987 | Edelman | 128/303.1 |
| 4,693,244 | 9/1987 | Daikuzono | 128/303.1 |
| 4,693,556 | 9/1987 | McCaughan | 350/320 |
| 4,718,056 | 1/1988 | Schultheiss | 350/96.18 |
| 4,726,648 | 2/1988 | Haberland et al. | 350/96.18 |
| 4,770,653 | 9/1988 | Shturman | 604/21 |
| 4,844,580 | 7/1989 | Lynch et al. | 350/96.18 |
| 4,846,172 | 7/1989 | Berlin | 128/303.1 |
| 4,846,544 | 7/1989 | Bortolin et al. | 350/96.18 |
| 4,848,339 | 7/1989 | Rink et al. | 128/303.1 |
| 4,854,315 | 8/1989 | Stack et al. | 128/303.1 |
| 4,989,944 | 2/1991 | Tholen et al. | 385/35 |
| 5,022,733 | 6/1991 | Angenent et al. | 350/96.18 |

OTHER PUBLICATIONS

Waltman et al., "Surgery of the Eye", Churchill Livingstone, N.Y., 1988.

Primary Examiner—John D. Lee
Assistant Examiner—Phan T. Heartney
Attorney, Agent, or Firm—Lowe, Price, LeBlanc & Becker

[57] ABSTRACT

Optical fiber devices for medical purposes and a method of making optical fiber devices. In one embodiment particularly suitable for laser surgery an optical fiber device is provided which includes an capsule which secures a lens element adjacent to an end of an optical fiber. The capsule includes fluid passageways which extend along the length thereof through which a temperature controlled fluid may be caused to flow. In another embodiment particularly suitable for providing a wide area of illumination an optical fiber device is provided which includes a main optical fiber element and a plurality of auxiliary optical fiber elements which are optically coupled thereto. The auxiliary optical fiber elements have terminal ends which project light that is transmitted through the main optical fiber.

18 Claims, 2 Drawing Sheets

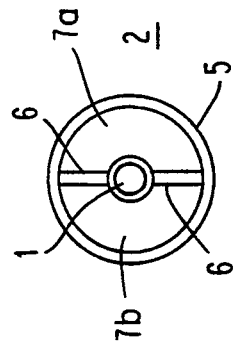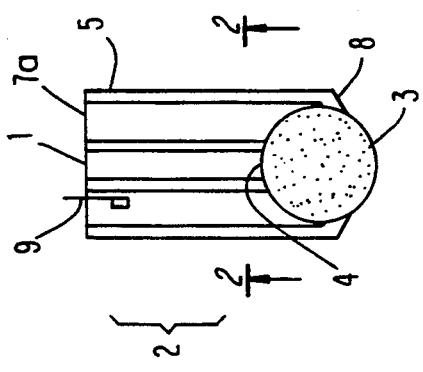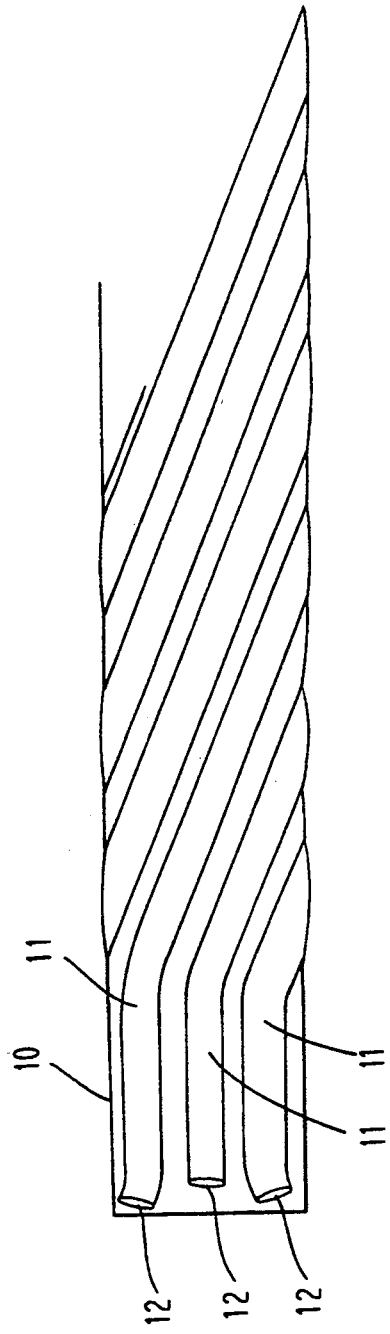

FOCUSING TIPS FOR OPTICAL FIBERS

TECHNICAL FIELD

The present invention relates to fiber optic devices for various medical uses and procedures. More particularly, the present invention relates to fiber optic devices which are useful for providing illumination light as well as therapeutic and/or surgical light energies.

BACKGROUND ART

Fiber optic devices have recently been developed and utilized for various medical applications involving examination and surgical procedures. Fiber optic devices have been utilized to provide illumination for examination purposes as well necessary illumination to view and perform surgical procedures.

In eye surgery procedures, the use of fiber optical illumination devices is often necessary inasmuch as there is a lack of natural illumination inside the eye. This is especially true in surgical procedures wherein the pupil is used for viewing, since no other natural ports for entering light exist. It has been proposed to utilize fiber optical devices to illuminate the inside of the eye during eye surgery and to utilize transocular and periocular laser delivery system for the treatment of eye diseases. For Example U.S. Pat. No. 4,846,172 to Berlin discloses a laser-delivery eye-treatment device and method.

The use of laser energy to abate atherosclerotic plaque that forms an obstruction in a blood vessel has recently become a viable alternative to coronary bypass surgery. This procedure, known as angioplasty, essentially involves the insertion of a fiber optical waveguide into the vessel, and the conduction of laser energy through the waveguide so as to direct the laser energy at the plaque once the distal end of the waveguide is positioned adjacent the obstruction.

A number of patents disclose various improvements to fiber optical devices which are designed for use in conjunction with lasers including: U.S. Pat. No. 4,854,315 to Stack et al; U.S. Pat. No. 4,848,339 to Rink et al; U.S. Pat. No. 4,770,653 to Shturman; U.S. Pat. No. 4,693,556 to McCaughan; U.S. Pat. No. 4,693,244 to Daikuzono; U.S. Pat. No. 4,681,104 to Edelman; and U.S. Pat. No. 4,641,912.

U.S. Pat. No. 4,290,667 discloses a fiber optical device in which a lens element 13 is cemented with a suitable polyester resin or epoxy 15 to a fibre end 14 which is positioned in a ferrule 11 (FIG. 1). Although lens 13 enables focusing of light energy, the manner in which the lens is cemented makes the lens subject to becoming detached from the fibre end, if excessively heated or as a result of a failure of the bonding cement.

The present invention provides for fiber optic devices which illuminate and provide for focusing of light energy in a manner which is an improvement over the prior art.

DISCLOSURE OF THE INVENTION

It is accordingly one object of the present invention to provide fiber optical devices for various surgical procedures.

Another object of the present invention is to provide fiber optical devices which are useful for providing illumination for medical examination and viewing surgical procedures.

A further object of the present invention is to provide fiber optical devices which provide a wide area of illumination.

A further object of the present invention is to provide fiber optical devices for laser surgical procedures.

A still further object of the present invention is to provide fiber optical devices which include lens elements.

A still further object of the present invention is to provide fiber optical devices which include internal temperature control means.

According to these and further objects of the present invention which will become apparent as the description thereof is presented below, the present invention provides an optical fiber device comprising an optical fiber, a lens positioned adjacent to an end of the optical fiber, and a capsule encasing the optical fiber and securing the focusing lens in position adjacent the optical fiber.

The present invention also provides for an optical fiber device comprising a main optical fiber element and a plurality of auxiliary optical fiber elements coupled to the main optical fiber element at one end thereof, each of the plurality of auxiliary optical fiber elements including a terminal end which projects light that is transmitted through the main optical fiber element.

Also provided for by the present invention is a method of producing an optical fiber device which comprises:

providing a main optical fiber element;

providing a plurality of auxiliary optical fiber elements;

positioning the plurality of auxiliary optical fiber elements adjacent the main optical fiber element along one end portion of the main optical fiber element;

aligning terminal ends of plurality of auxiliary optical fiber elements; and optically coupling the plurality of auxiliary optical fiber elements to the main optical fiber element.

BRIEF DESCRIPTION OF DRAWINGS

The present invention will be described with reference to the annexed drawings which are given by way of non-limiting examples only, in which:

FIG. 1 is a sectional view of a fiber optical device according to one embodiment of the present invention.

FIG. 2 is a sectional view taken along lines 2—2 of FIG. 1.

FIG. 3 is a side view illustrating a fiber optical device according to another embodiment of the present invention.

BEST MODE FOR CARRYING OUT THE INVENTION

Figure 4:
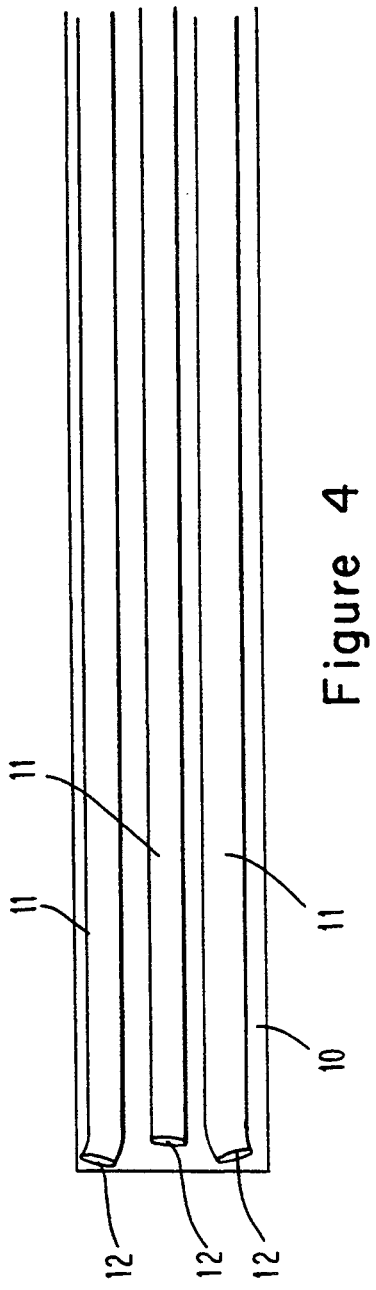
FIG. 4 is a side view illustrating an initial step involved in manufacturing the fiber optical device of FIG. 3.

The present invention is directed to fiber optical devices which are capable of either focusing light energy or distributing light on a desired, normally inaccessible location within a subject's body. Generally, the fiber optical devices of the present invention comprise a length of an optical fiber and a tip assembly which is fixed to a distal end of the optical fiber. The design of the tip assembly according to the present invention determines whether the fiber optical device provides a focused light energy beam, e.g. a laser or sharp illumination beam, or whether the fiber optical device provides a broad illumination beam.

The fiber optical devices of the present invention are useful for delivering various types of light to normally inaccessible locations in a subject's body. For example, the fiber optical devices of the present invention may be utilized to deliver laser light to a location within the body for surgical purposes, e.g., to remove obstructions in blood vessels as in the case of laser angioplasty. The fiber optical devices of the present invention may also be utilized to deliver necessary light for photodynamic therapy as in the case of cancer treatment. In further applications, the fiber optical devices of the present invention may be utilized to deliver low or medium intensity illumination light for purposes of examination and/or viewing surgical procedures as in the case of intraocular surgery of the eye.

The optical fiber portion of the fiber optical devices of the present invention should be of a sufficient length to extend between a light source and a site to which light is to be directed. The optical fiber may be made from any conventional material utilized for making light conducting optical fibers including glass, quartz, silica, sapphire, or any conventional light transmitting material. In addition, the optical fiber portion may include a cladding portion in a known manner.

In the case in which it is desired to provide a focused light source, e.g., a focused laser, the tip assemble of the optical fiber devices according to the present invention provides a means to secure a suitable lens or ball element on or adjacent to a distal end of the optical fiber portion. In a preferred embodiment, a focusing lens or ball is provided. However, it is to be understood that any suitable lens element could be incorporated.

FIG. 1 is a sectional view of a fiber optical device according to one embodiment of the present invention which includes an optical fiber portion 1 and a capsule portion 2 which serves as a means to secure a lens or ball element 3 on or adjacent a distal end 4 of the optical fiber 1. In a preferred embodiment, the lens or ball element 3 is utilized to focus light, e.g., laser light which is transmitted through the optical fiber 1.

The capsule portion 2 comprises a generally cylindrical casing 5 in which the optical fiber 1 is centrally positioned. As illustrated in FIG. 2, a pair of diametrically opposed partition members 6 are connected between the cylindrical casing 5 of the capsule portion 2 and the optical fiber 1 to maintain the position of the optical fiber 1 within the capsule portion. Moreover, as discussed below, the partition members 6 which extend along the length of the optical fiber 1 and capsule portion 2 define fluid passages 7a and 7b through which a temperature controlled fluid, e.g., a saline solution, may be caused to flow.

The end of the capsule portion 2 includes a tapered portion 8 which encapsulates all but a distal portion of lens or ball element 3. In a preferred embodiment, the capsule portion 2 is made from a metal which is biocompatible, e.g. surgical steel. However, it is possible to make the capsule portion 2 from any suitable rigid biocompatible material, e.g., plastic or resinous material. Preferably, the capsule portion 2 is made from a material which also prevents light from scattering out from the sides of the optical fiber 1.

The lens or ball element 3 is preferably spherical and free to rotate. In other embodiments, the lens may be other than spherical, in which case the lens will not be rotatable. The lens or ball element 3 may be made from any light transmitting material and may be made of the same material as optical fiber 1 or may be made of a different material. In one embodiment according to the present invention a sapphire focusing ball was found to be particular useful. As can be appreciated, by utilizing the capsule portion 2 to secure the lens or ball element 3 adjacent the distal end 4 of the optical fiber 1 the fiber optical devices of the present invention can utilize lens or ball elements which are made from a material which is dissimilar to the material from which the optical fiber 1 is made. Thus, the present invention is distinguishable from a number of prior known devices which merely melt and form thereby a lens element on the end of optical fibers.

FIG. 2 is a sectional view taken along lines 2—2 of FIG. 1. As discussed above, FIG. 2 depicts partition members 6 which extend along the entire length of capsule portion 2 and optical fiber 1, so as to define fluid passages 7a and 7b. In one mode of preferred operation, a temperature controlled fluid such as a saline solution (or gas) is feed through one of fluid passages 7a or 7b and withdrawn from the other at an end of the device which is opposite that at which the lens or ball element 3 is secured. In this manner, during use, e.g., during laser surgery, it is possible to pass a cooling fluid through the device and thereby prevent over heating or excessive heating which may be damaging to adjacent tissue. In a further preferred embodiment temperature sensors 9 may be provided in either or both of the fluid passages to precisely monitor the temperature of the focusing lens or ball to ensure that no over-heating occurs.

It is noted that the use of two partition members 6 represents a minimum needed to provide two fluid passages and that three, or four, or more partition members may be used in which case the number of fluid passages would also increase. In such an embodiment the temperature controlled fluid or gas could be passed through one or more of the fluid passages provided at least one fluid passage is reserved for withdrawing the temperature controlled fluid.

FIG. 3 is a side view of a fiber optical device according to another embodiment of the present invention. The embodiment depicted in FIG. 3, as will be described in detail below, provides for a wide angle of illumination which is useful for examination purposes and particularly suitable viewing surgical procedures such as intraocular surgery of the eye.

The fiber optical device depicted in FIG. 3 includes a main delivery fiber 10 and a plurality of auxiliary fibers 11 which provide a composite illumination angle that is proportional to the total number of fibers. That is, the viewing angles of each fiber are additive and result in illumination angle that is wider than that which can be obtained with a single fiber.

As in the case of the optical fiber device depicted in FIG. 1, both the main fiber 10 and auxiliary fibers 11 utilized in the embodiment depicted in FIG. 3 may be made from materials which are conventionally utilized in making optical fibers, i.e., glass, quartz, silica, and the like. As will become apparent from the manner in which the device in FIG. 3 is made, as described below in reference to FIGS. 4 and 5 below, it is preferred that the main fiber 10 and auxiliary fibers 11 are made from the same material.

In general, the optical fiber device in FIG. 3 includes the main fiber 10 which may be of any desired length. The main fiber 10 is coupled at one end to a suitable light source, e.g., a laser, in a known manner and serves to transmit light to the distal end which is shown in FIG. 3. The auxiliary fibers 11 are formed to be integral with the main fiber 10 in the manner described below. The auxiliary fibers 11 provide a number of terminal ends 12 which distribute light which is transmitted through the main fiber 10. Accordingly, the greater the number of auxiliary fibers, the greater or wider the area of illumination.

The manner in which the terminal ends 12 of the auxiliary fibers 11 are aligned on the main fiber 10 is essentially unlimited. In this regard, each of the terminal ends 12 of the auxiliary fibers 11 may be individually aligned to provide a desired angle of illumination. Thus, the auxiliary fibers 11 may be equally spaced around the main fiber 10 and the terminal ends may be similarly aligned so as to provide a uniform illumination angle. In one exemplary device having six auxiliary fibers 11 which were equally positioned around the main fiber 10 and had terminal ends 12 which were similarly aligned and provided individual illumination angles of 30° the resulting device have a total illumination angle of 180° which is six times greater than that which can be obtained with a single fiber.

It is to be particularly noted that the terminal ends 12 of the auxiliary fibers 11 do not have to be cut at a beveled angle so as to direct transmitted light at an angle with respect to the central axis of the auxiliary fibers 11. In this regard, the flat terminal ends 12 are individually aimed or aligned in a desired angle as illustrated in FIG. 3. In this manner, the optical fiber device may be more efficiently fabricated in the manner described below.

As depicted and understood from the description provided herein, the auxiliary fibers 11 are substantially smaller in diameter that the main fiber 10 when more that six auxiliary fibers 11 are utilized so that the auxiliary fibers 11 may be positioned around the main fiber 10 while maintaining the composite diameter of the device suitable small for a desired use, e.g., passage in the pars plana for eye surgery. When utilizing six or less auxiliary fibers 11, the diameter of the auxiliary fibers 11 and main fiber 10 may be the same, with the proviso that the composite diameter of the device be suitable small for a desire use.

Figure 5:
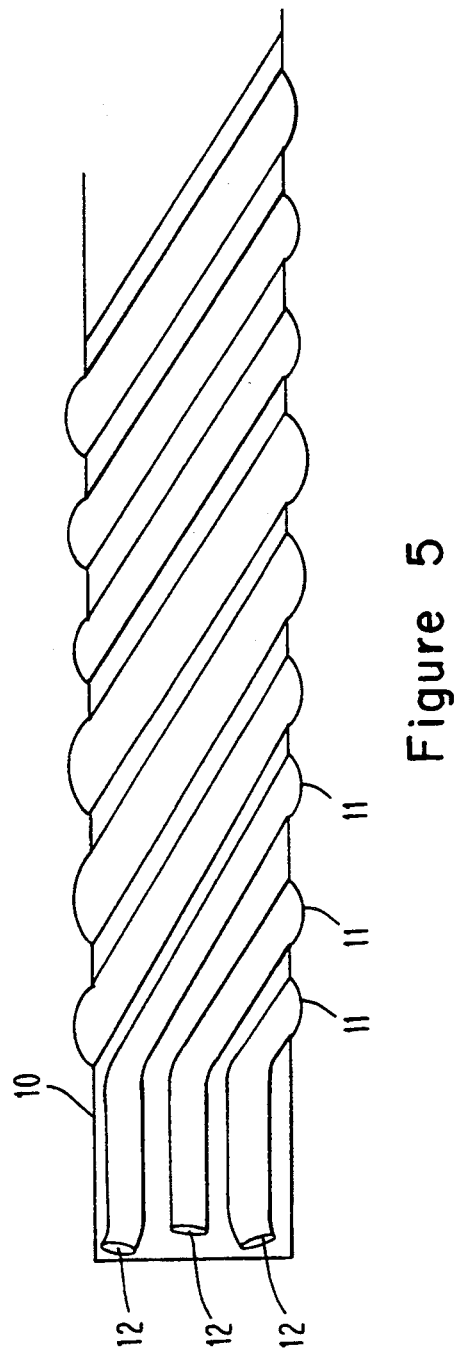
FIG. 5 is a side view illustrating an intermediate step involved in manufacturing the fiber optical device of FIG. 3.

FIGS. 4 and 5 illustrate the general manner in which the optical fiber device of FIG. 3 is made. FIG. 4 illustrates an initial step used in manufacturing the optical fiber device. FIG. 5 illustrates an intermediate step used in manufacturing the optical fiber device.

In making the device illustrated in FIG. 3, the main fiber 10 is selected to have a sufficient length to reach from a light source which may be a laser or other source of light to the site at which the illumination is to be provided, e.g., a surgical site or examination site. Generally, the main fiber 10 is a few meters in length at most.

The main fiber 10 is first inserted in the center of a rotatable fixture such as a glass lathe. Next, the auxiliary fibers 11 are arranged around the main fiber 10 and have their terminal ends 12 angularly aligned to provide for a desired emission angle in the final device. Once the auxiliary fibers 11 are positioned and have their terminal ends 12 angularly aligned, they are thereafter held in position during the remainder of the manufacturing process.

The device which holds the auxiliary fibers 11 in position should be designed to be rotatable around the main fiber 10, independently of the rotation of the entire unit so that the auxiliary fibers 11 can be wrapped around the main fiber as illustrated in FIG. 5. In addition to being able to wrap the auxiliary fibers 11 around the main fiber 10, the device which holds all the fibers should be extendable along the axis of the main fiber 10 so as to stretch the fibers as described below.

Once the fibers are assembled in the glass lathe device and arranged as illustrated in FIG. 4, the fibers are carefully heated, for example by a hot hydrogen-oxygen torch, at the point where it is desired to optically couple the fibers. At first, heat is applied to remove any outer protective coating or cladding, of the fibers. Alternatively, any protective coating or cladding may be first removed mechanically or chemically at an earlier stage.

After the outer protective coating or cladding is removed, the temperature is raised to heat the fibers to their melting temperature. Simultaneously, the auxiliary fibers 11 are wrapped around the main fiber 10 as illustrated in FIG. 5 and stretched to make all the fibers thinner at the coupling point. Heat is then slowly removed or maintained for a period of time at a lower temperature to anneal the entire structure and ensure homogeneous optical properties at the coupling point between all of the fibers.

After coupling and optically annealing the fibers, the auxiliary fibers 11 are trimmed at the point of coupling. That is, the only portion of the auxiliary fibers 11 which is retained in the final device is the portion thereof between the coupling portion and the terminal ends 12.

After coupling, the coupling portion is strengthened by adding thereto glass, epoxy or any other suitable coating material to preserve the alignment of the terminal ends 12 of the auxiliary fibers 11.

As a final step, the entire assembly is threaded into the head of an appropriately sized needle or catheter for surgical or other medical use.

Although the present invention has been described with reference to particular means, materials and embodiments, from the foregoing description, one skilled in the art can easily ascertain the essential characteristics of the present invention and various changes and modifications may be made to adapt the various uses and characteristics without departing from the spirit and scope of the present invention as described by the claims that follow.

What is claimed is:

1. An optical fiber device comprising an optical fiber, a lens positioned adjacent to an end of said optical fiber, and a capsule encasing said optical fiber and securing said lens in position adjacent said optical fiber, said capsule comprising an inward tapered portion at an end thereof which contacts and encompasses all but a distal portion of said lens, said inward tapered portion of said capsule being such that an inner diameter of said capsule decreases in the direction of said end thereof, and said capsule being spaced from the optical fiber to form an annular space therebetween which annular space includes at least two fluid passages which extend along the length thereof.

2. An optical fiber device according to claim 1, wherein said capsule is made from a material which prevents light from scattering out from the sides of the optical fiber.

3. An optical fiber according to claim 2, wherein said capsule is made from metal.

4. An optical fiber device according to claim 1, wherein said lens comprises a spherical lens which is free to rotate within said capsule.

5. An optical fiber device according to claim 1, wherein said optical fiber and said lens are made from dissimilar materials.

6. An optical fiber device according to claim 1, wherein said lens comprises a focusing lens.

7. An optical fiber device comprising a main optical fiber element and a plurality of auxiliary optical fiber elements coupled to said main optical fiber element and extending along one end portion thereof, each of said plurality of auxiliary optical fiber elements including a terminal end which projects light that is transmitted through said main optical fiber element.

8. An optical fiber device according to claim 7, wherein said plurality of auxiliary optical fiber elements comprises more than six auxiliary optical fiber elements.

9. An optical fiber device according to claim 7, wherein said plurality of auxiliary optical fibers are equally spaced about the main optical fiber element.

10. An optical fiber device according to claim 7, wherein said terminal ends of said plurality of auxiliary optical fibers are similarly angularly aligned with respect to the central axis of said main optical fiber element and held in said angularly alignment.

11. An optical fiber device according to claim 7, wherein said plurality of auxiliary optical fiber elements are wrapped around said main optical fiber element where the optical fiber elements are coupled.

12. An optical fiber device according to claim 11, wherein said plurality of auxiliary optical fiber elements are coupled to main optical fiber element by a heat treating method which includes an optical annealing step.

13. An optical fiber device according to claim 7, wherein said plurality of auxiliary optical fiber elements comprises up to six auxiliary optical fiber elements.

14. A method of producing an optical fiber device which comprises:
providing a main optical fiber element;
providing a plurality of auxiliary optical fiber elements;
positioning said plurality of auxiliary optical fiber elements adjacent said main optical fiber element along one end portion of said main optical fiber element;
aligning terminal ends of plurality of auxiliary optical fiber elements; and
optically coupling said plurality of auxiliary optical fiber elements to said main optical fiber element.

15. A method of producing an optical fiber device according to claim 14, wherein said terminal ends of said plurality of auxiliary optical fiber elements are flat.

16. A method of producing an optical fiber device according to claim 14, wherein said optical coupling step comprises heating said main and said plurality of optical fiber elements to a temperature sufficient to melt said fibers while simultaneously wrapping said plurality of auxiliary optical fiber elements around said main optical fiber element and stretching the resulting optical fiber assembly.

17. A method of producing an optical fiber device according to claim 16, wherein said optical coupling step further comprises thermally annealing said optical fiber assembly.

18. A method of producing an optical fiber device according to claim 17, further comprising coating said optical fiber assembly where said optical coupling is effected with a material that strengthens said coupling.

* * * * *